(12) United States Patent
Locke (10) Patent No.: US 11,826,234 B2
(45) Date of Patent: Nov. 28, 2023

(54) DISTRIBUTED NEGATIVE PRESSURE WOUND THERAPY SYSTEM INCORPORATING AN ABSORBENT DRESSING AND PIEZO-ELECTRIC PUMP

(71) Applicant: KCI LICENSING, INC., San Antonio, TX (US)

(72) Inventor: Christopher B. Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 282 days.

(21) Appl. No.: 17/255,095

(22) PCT Filed: Jun. 14, 2019

(86) PCT No.: PCT/US2019/037190
§ 371 (c)(1),
(2) Date: Dec. 22, 2020

(87) PCT Pub. No.: WO2020/005577
PCT Pub. Date: Jan. 2, 2020

(65) Prior Publication Data
US 2021/0260273 A1    Aug. 26, 2021

Related U.S. Application Data

(60) Provisional application No. 62/691,429, filed on Jun. 28, 2018.

(51) Int. Cl.
*A61F 13/00* (2006.01)
*A61M 1/00* (2006.01)
*A61F 13/02* (2006.01)

(52) U.S. Cl.
CPC .... *A61F 13/00068* (2013.01); *A61F 13/0206* (2013.01); *A61F 13/0216* (2013.01);
(Continued)

(58) Field of Classification Search
CPC .......... A61M 2230/65; A61M 2209/00; A61M 2209/01; A61M 2209/06; A61M 2209/08;
(Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Erich G Herbermann
*Assistant Examiner* — Seth Han (57) ABSTRACT

A negative pressure wound therapy system includes a wound dressing, at least one pump fluidly coupled to the fluid interface, a pressure sensor fluidly coupled to the wound dressing, a control housing, and an electrical coupler. The wound dressing includes a sealing layer, an absorbent layer adjacent to the sealing layer, and a fluid interface attached to at least one of the sealing layer or the absorbent layer. The at least one pump is configured to apply negative pressure to the fluid interface to draw fluid from the wound dressing via the fluid interface. The pressure sensor is configured to detect a fluid pressure of the wound dressing. The control housing is remote from the wound dressing. The electrical
(Continued)

coupler is configured to removably connect the control housing to the at least one pump.

13 Claims, 5 Drawing Sheets (52) U.S. Cl.
CPC .............. *A61M 1/74* (2021.05); *A61M 1/884* (2021.05); *A61M 1/915* (2021.05); *A61M 1/95* (2021.05); *A61M 1/962* (2021.05); *A61M 1/966* (2021.05); *A61F 2013/0028* (2013.01); *A61M 1/73* (2021.05); *A61M 1/732* (2021.05); *A61M 1/80* (2021.05); *A61M 1/985* (2021.05); *A61M 2205/0294* (2013.01); *A61M 2205/18* (2013.01); *A61M 2205/3324* (2013.01); *A61M 2205/3327* (2013.01); *A61M 2205/3344* (2013.01); *A61M 2205/3368* (2013.01); *A61M 2205/7518* (2013.01); *A61M 2205/8256* (2013.01)

(58) Field of Classification Search
CPC ...... A61M 2209/086; A61M 2209/088; A61M 1/90; A61M 1/95; A61M 1/962; A61M 1/966; A61M 2205/8206; A61M 2205/82; A61M 2205/8237
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A * | 5/1989 | Richmond .............. A61M 1/79 604/323 |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,562,621 A * | 10/1996 | Claude ............ A61M 25/10188 604/100.03 |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,838,717 B2 | 11/2010 | Haggstrom et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2012/0053541 A1* | 3/2012 | Yao .......................... A61M 1/79 604/319 |
| 2014/0039426 A1 | 2/2014 | Coulthard et al. |
| 2015/0174304 A1* | 6/2015 | Askem ............ A61F 13/00042 604/319 |
| 2017/0112974 A1* | 4/2017 | Fujisaki ................ A61M 1/962 |
| 2018/0078686 A1* | 3/2018 | Proctor, Jr. ........ A61F 13/00068 |
| 2019/0348216 A1* | 11/2019 | Kim ........................ H01F 27/40 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| DE | 29 504 378 U1 | 9/1995 | |
|---|---|---|---|
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2018060412 A1 * | 4/2018 | ....... A61F 13/00068 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and written Opinion in International Application No. PCT/US2019/037190, dated Sep. 26, 2019.

\* cited by examiner

DISTRIBUTED NEGATIVE PRESSURE WOUND THERAPY SYSTEM INCORPORATING AN ABSORBENT DRESSING AND PIEZO-ELECTRIC PUMP

CROSS-REFERENCE TO RELATED APPLICATIONS

This application claims the benefit of priority to international patent application number PCT/US2019/037190, filed on Jun. 14, 2019, which claims the benefit of priority to U.S. Provisional Application No. 62/691,429, filed on Jun. 28, 2018, the complete disclosures of which are incorporated herein by reference in their entireties.

BACKGROUND

The present disclosure relates generally to wound therapy systems and devices, and more particularly to a distributed negative pressure wound therapy system incorporating an absorbent dressing and piezo-electric pump and related apparatuses and methods.

Negative pressure wound therapy (NPWT) is a type of wound therapy that involves applying negative pressure (relative to atmosphere pressure) to a wound site, via a wound dressing, to promote wound healing. Some NPWT systems include a pump which operates to maintain the wound site at negative pressure by removing wound exudate from the wound site via the wound dressing.

SUMMARY

One implementation of the present disclosure is a negative pressure wound therapy system. The system includes a wound dressing module including a sealing layer, an absorbent layer adjacent to the sealing layer, and a fluid interface attached to at least one of the sealing layer or the absorbent layer. The system includes a pump and pressure sensing module disposed on the wound dressing module. The pump and pressure sensing module includes at least one pump fluidly coupled to the fluid interface, the at least one pump configured to apply negative pressure to the fluid interface to draw fluid from the wound dressing via the fluid interface and a pressure sensor fluidly coupled to the wound dressing module, the pressure sensor configured to detect a fluid pressure of the wound dressing module. The system includes a control and power module removably coupled to and remote from the pump and pressure sensing module. The control and power module includes a control housing and an electrical coupler configured to connect the control housing to the at least one pump.

In some embodiments, the control housing includes a first receiver body defining a power reception interface, and the control and power module includes a power housing sized to be at least partially received within the first receiver body of the control housing, the power housing including a power delivery interface configured to removably couple to the power reception interface of the control housing and a power supply configured to provide power to the at least one pump via the power delivery interface, the power reception interface, and the electrical coupler.

In some embodiments, the absorbent layer includes at least one of (1) a wicking layer adjacent to a super-absorber or (2) a first layer of three-dimensional textile and a second layer of a non-woven super-absorber.

In some embodiments, the absorbent layer includes a hydrophilic foam.

In some embodiments, the system includes a perforated layer adjacent to the sealing layer.

In some embodiments, the fluid interface includes a filter that is at least one of hydrophobic or configured to filter bacteria.

In some embodiments, the system includes a cover layer including a film, the absorbent layer disposed between the sealing layer and the cover layer. The system can include a thermal dissipation layer disposed between the cover layer and the absorbent layer.

In some embodiments, the at least one pump includes a piezoelectric pump.

In some embodiments, the at least one pump and the pressure sensor are mounted to a flexible electronics module. In some embodiments, the flexible electronics module includes at least one of a thermistor, an accelerometer, or a pH sensor. In some embodiments, the flexible electronics module includes a status indicator.

In some embodiments, the system includes a housing configured to at least partially enclose the flexible electronics module, the at least one pump, and the pressure sensor, the housing attached to the wound dressing module. The control and power module can be separate from and outside the housing. In some embodiments, the system includes an exhaust interface configured to receive exhaust air from the at least one pump and at least one of (1) transfer the received exhaust air outside of the housing or (2) transfer the exhaust air to the wound dressing to assist evaporation of fluid in the wound dressing.

In some embodiments, the electrical coupler is configured to transmit at least one electrical signal indicating a status parameter to the control housing, the status parameter including at least one of a pressure, a temperature, an orientation, or a pH. In some embodiments, the system includes a processing circuit configured to receive the at least one electrical signal and convert the at least one electrical signal into a multiplexed signal for transmission to the power housing via the electrical coupler.

In some embodiments, the electrical coupler includes a conductive wire ribbon.

In some embodiments, wherein the power housing includes a communications circuit configured to output a communication signal based on data received via the electrical coupler.

In some embodiments, the power housing includes an alarm circuit configured to detect an impedance load of the electrical coupler and output an indication of an alarm condition based on the impedance load indicating that the power housing is in an activated state and is not coupled to the at least one pump by the electrical coupler.

In some embodiments, the power supply has a capacity sufficient to cause the pump to output a vacuum pressure of at least 100 mmHg for a duration of at least 6 hours and a leak condition of at least 20 cubic centimeters per minute.

In some embodiments, the control housing includes a recharge interface operably connected to the power reception interface.

Another implementation of the present disclosure is a negative pressure wound therapy system. The system includes a wound dressing including a sealing layer, an absorbent layer adjacent to the sealing layer, and a fluid interface attached to at least one of the sealing layer or the absorbent layer. The system includes at least one pump fluidly coupled to the fluid interface, the at least one pump configured to apply negative pressure to the fluid interface to draw fluid from the wound dressing via the fluid interface, and a pressure sensor fluidly coupled to the wound dressing, the pressure sensor configured to detect a fluid pressure of the wound dressing. The system includes a control housing remote from the wound dressing and an electrical coupler configured to removably connect the control housing to the at least one pump.

In some embodiments, the control housing includes a first receiver body defining a power reception interface, and the negative wound pressure therapy system includes a power housing sized to be at least partially received within the first receiver body of the control housing, the power housing including a power delivery interface configured to removably couple to the power reception interface of the control housing and a power supply configured to provide power to the at least one pump via the power delivery interface, the power reception interface, and the electrical coupler.

In some embodiments, the absorbent layer includes at least one of (1) a wicking layer adjacent to a super-absorber or (2) a first layer of three-dimensional textile and a second layer of a non-woven super-absorber.

In some embodiments, the absorbent layer includes a hydrophilic foam.

In some embodiments, the system includes a perforated layer adjacent to the sealing layer.

In some embodiments, the fluid interface includes a filter that is at least one of hydrophobic or configured to filter bacteria.

In some embodiments, the system includes a cover layer including a film, the absorbent layer disposed between the sealing layer and the cover layer. The system can include a thermal dissipation layer disposed between the cover layer and the absorbent layer.

In some embodiments, the at least one pump includes a piezoelectric pump.

In some embodiments, the at least one pump and the pressure sensor are mounted to a flexible electronics module. In some embodiments, the flexible electronics module includes at least one of a thermistor, an accelerometer, or a pH sensor. In some embodiments, the flexible electronics module includes a status indicator. In some embodiments, the system includes a housing configured to at least partially enclose the flexible electronics module, the at least one pump, and the pressure sensor, the housing attached to the wound dressing module. In some embodiments, the system includes an exhaust interface configured to receive exhaust air from the at least one pump and at least one of (1) transfer the received exhaust air outside of the housing or (2) transfer the exhaust air to the wound dressing to assist evaporation of fluid in the wound dressing.

In some embodiments, the electrical coupler is configured to transmit at least one electrical signal indicating a status parameter to the control housing, the status parameter including at least one of a pressure, a temperature, an orientation, or a pH. In some embodiments, the system includes a processing circuit configured to receive the at least one electrical signal and convert the at least one electrical signal into a multiplexed signal for transmission to the power housing via the electrical coupler.

In some embodiments, the electrical coupler includes a conductive wire ribbon.

In some embodiments, wherein the power housing includes a communications circuit configured to output a communication signal based on data received via the electrical coupler.

In some embodiments, the power housing includes an alarm circuit configured to detect an impedance load of the electrical coupler and output an indication of an alarm condition based on the impedance load indicating that the power housing is in an activated state and is not coupled to the at least one pump by the electrical coupler.

In some embodiments, the power supply has a capacity sufficient to cause the pump to output a vacuum pressure of at least 100 mmHg for a duration of at least 6 hours and a leak condition of at least 20 cubic centimeters per minute.

In some embodiments, the control housing includes a recharge interface operably connected to the power reception interface.

Another implementation of the present disclosure is a method of operating a negative pressure wound therapy system. The method includes connecting an electrical coupler to a control housing and to at least one pump, the control housing comprising a first receiver body defining a power reception interface, the at least one pump fluidly coupled to a fluid interface of a wound dressing to draw fluid from the wound dressing via the fluid interface; receiving a power housing at least partially within the first receiver body to connect a power delivery interface of the power housing to the power reception interface; and providing power from a power supply of the power housing to the at least one pump via the power delivery interface, the power reception interface, and the electrical coupler.

In some embodiments, the method includes outputting a status of the at least one pump using a status indicator coupled to the at least one pump.

In some embodiments, the method includes transmitting, from a first processing circuit attached to the wound dressing to a second processing circuit of the control housing via the electrical coupler, at least one electrical signal indicating a status parameter to the control housing, the status parameter including at least one of a pressure, a temperature, an orientation, or a pH. Transmitting the at least one electrical signal can include converting a plurality of status signals into a multiplexed signal.

In some embodiments, the method includes detecting, by an alarm circuit of the control housing, an impedance load of the electrical coupler, and outputting an indication of an alarm condition based on the impedance load indicating that the power housing is in an activated state and is not coupled to the at least one pump by the electrical coupler.

Another implementation of the present disclosure is a method of using a negative pressure wound therapy system. The method includes attaching a wound dressing to a wound site of a patient, the wound dressing including a sealing layer, an absorbent layer adjacent to the sealing layer, and a fluid interface attached to at least one of the sealing layer or the absorbent layer; coupling at least one pump to the fluid interface to apply negative pressure to the fluid interface draw fluid from the wound dress via the fluid interface; attaching a control housing to a wearable device on the patient remote from the at least one pump and the wound dressing; and connecting an electrical coupler to the control housing and to the at least one pump.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the FIGURES, a distributed negative pressure wound therapy (NPWT) system and components thereof are shown, according to various exemplary embodiments. In some embodiments, a distributed NPWT system includes a wound dressing module including a sealing layer, an absorbent layer adjacent to the sealing layer, and a fluid interface attached to at least one of the sealing layer or the absorbent layer. The system includes a pump and pressure sensing module disposed on the wound dressing module. The pump and pressure sensing module includes at least one pump fluidly coupled to the fluid interface, the at least one pump configured to apply negative pressure to the fluid interface to draw fluid from the wound dressing via the fluid interface and a pressure sensor fluidly coupled to the wound dressing module, the pressure sensor configured to detect a fluid pressure of the wound dressing module. The system includes a control and power module removably coupled to and remote from the pump and pressure sensing module. The control and power module includes a control housing and an electrical coupler configured to connect the control housing to the at least one pump. In some embodiments, the system includes a power housing sized to at least partially be received within a first receiver body of the control housing. The power housing includes a power delivery interface configured to removably couple to a power reception interface of the control housing, and a power supply configured to provide power to the at least one pump via the power delivery interface, the power reception interface, and the electrical coupler.

In some embodiments, the NPWT system can enable the use of silent pumps, such as piezoelectric pumps mounted on the wound dressing, while reducing the inefficiencies associated with the use of such pumps. In existing systems, piezoelectric pumps may be used due to their silent (or near-silent) operation, which can improve the user experience. However, to achieve target pressures, including addressing leaks at target pressure, may require battery-based power supplies with relatively high capacity, which may be associated with relatively high weight and heat generation. The present solution can improve upon existing system by allowing the at least one pump to be mounted to the wound dressing (and thus to the patient-mounted portion of the NPWT system) while control electronics can be remote from the wound dressing and the power supply can be decoupled from the wound dressing for re-charging; in addition, heat generation can be effectively managed using thermal dissipation layer(s) in the wound dressing that can direct heat generation towards fluid evaporation rather than towards the patient's skin.

Distributed Negative Pressure Wound Therapy System

Referring now to FIGS. 1-4, a distributed negative pressure wound therapy (NPWT) system 100 is shown, according to an exemplary embodiment. The distributed NPWT system 100 includes a wound dressing module 200, a pump and pressure sensing module 300 that can be disposed on the wound dressing module 200, and a control and power module 400 that can be removably coupled to the pump and pressure sensing module 300.

Figure 2:
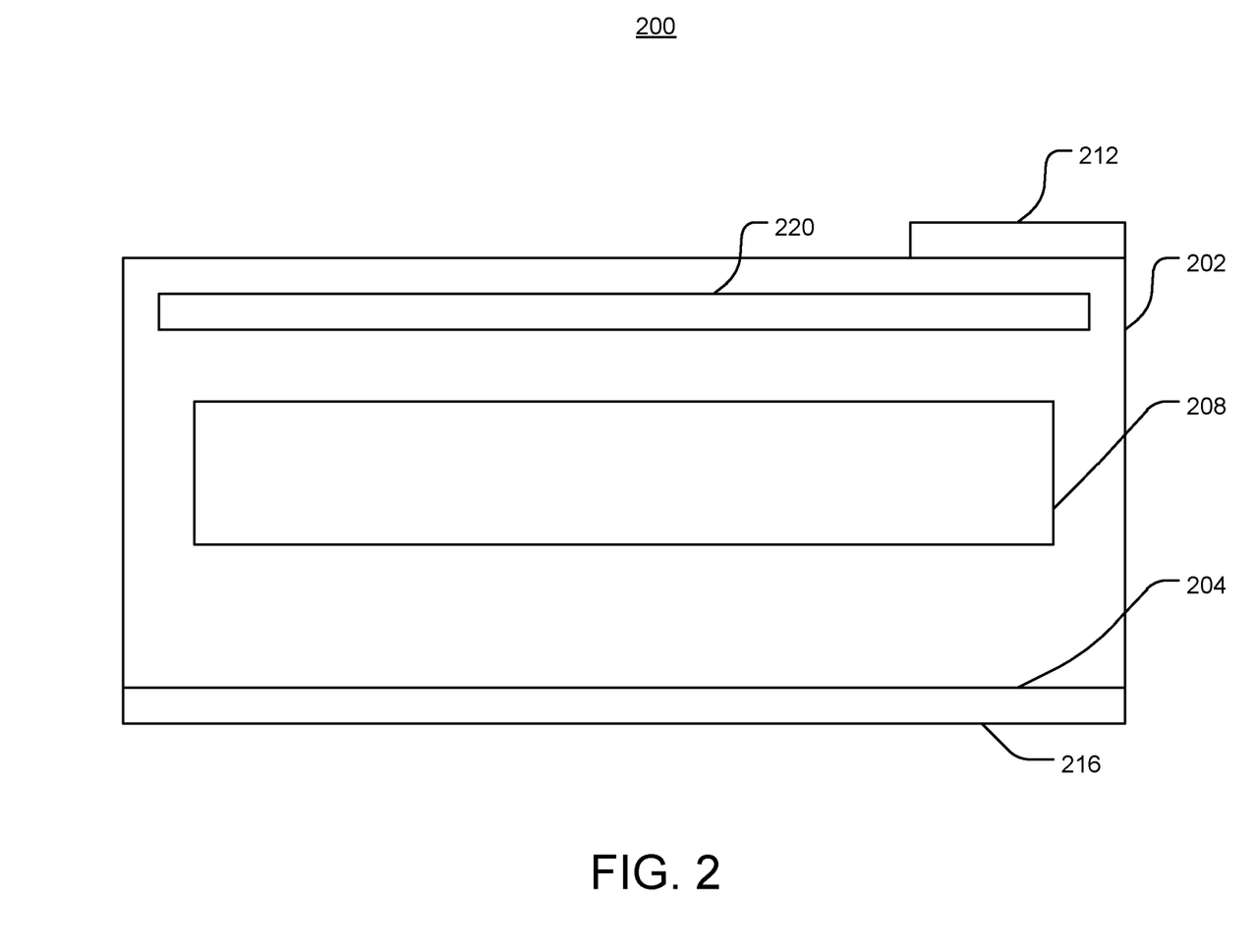
FIG. 2 is a block diagram illustrating a wound dressing module of the distributed NPWT system of FIG. 1, according to an exemplary embodiment.

The wound dressing module 200 can be disposed at a wound site 106. Wound site 106 may include a tissue wound as well as a wound dressing (of the wound dressing module 200) that covers the tissue wound and adheres to a patient's skin.

In some embodiments, the wound dressing module 200 includes a sealing layer 204, an absorbent layer 208 adjacent to the sealing layer 204, and a fluid interface 212 attached to at least one of the sealing layer 204 or the absorbent layer 208. The wound dressing module 200 can include an outer cover layer housing 202. The cover layer 202 can include a film.

The sealing layer 204 can include an adhesive (e.g., on a periphery of the sealing layer 204) to adhere the wound dressing module 200 to the patient's skin. The adhesive can include at least one of an acrylic material or a silicone material (e.g., DERMATAC). The adhesive can include a flange of acrylic material. The adhesive can include a plurality of adhesive strips. The adhesive can include a selectively adhesive material, such as an adhesive material that changes to an adhesive state based on exposure to temperature and/or ultraviolet (UV) light-based conditions (e.g., a UV adhesive material including a light-blocking material). The adhesive can be provided in sections to enable increased ease of bend and expansion (e.g., as compared to printed adhesive) as well as fluid evaporation.

The sealing layer 204 can include or be adjacent to a perforated layer 216. The perforated layer 216 can provide fluid channels for fluid in the wound dressing module 200 to be transported through the sealing layer 204 into the absorbent layer 208. The sealing layer 204 can include at least one of a hydrogel or hydrocolloid material.

The absorbent layer 208 can include a wicking layer adjacent to a super-absorber. The absorbent layer 208 can include a first layer of three-dimensional textile and a second layer of a non-woven super-absorber. The absorbent layer can include a hydrophilic foam (e.g., AMS, Freudenburg foams having a thickness greater than or equal to 0.5 millimeter and less than or equal to 4 millimeter; a foamed hydrofiber). The absorbent layer 208 can include a wicking layer (e.g., LIBELTEX) surrounding a super-absorber (e.g., TEXUS; BASF LUQUAFLEECE).

Figure 3:
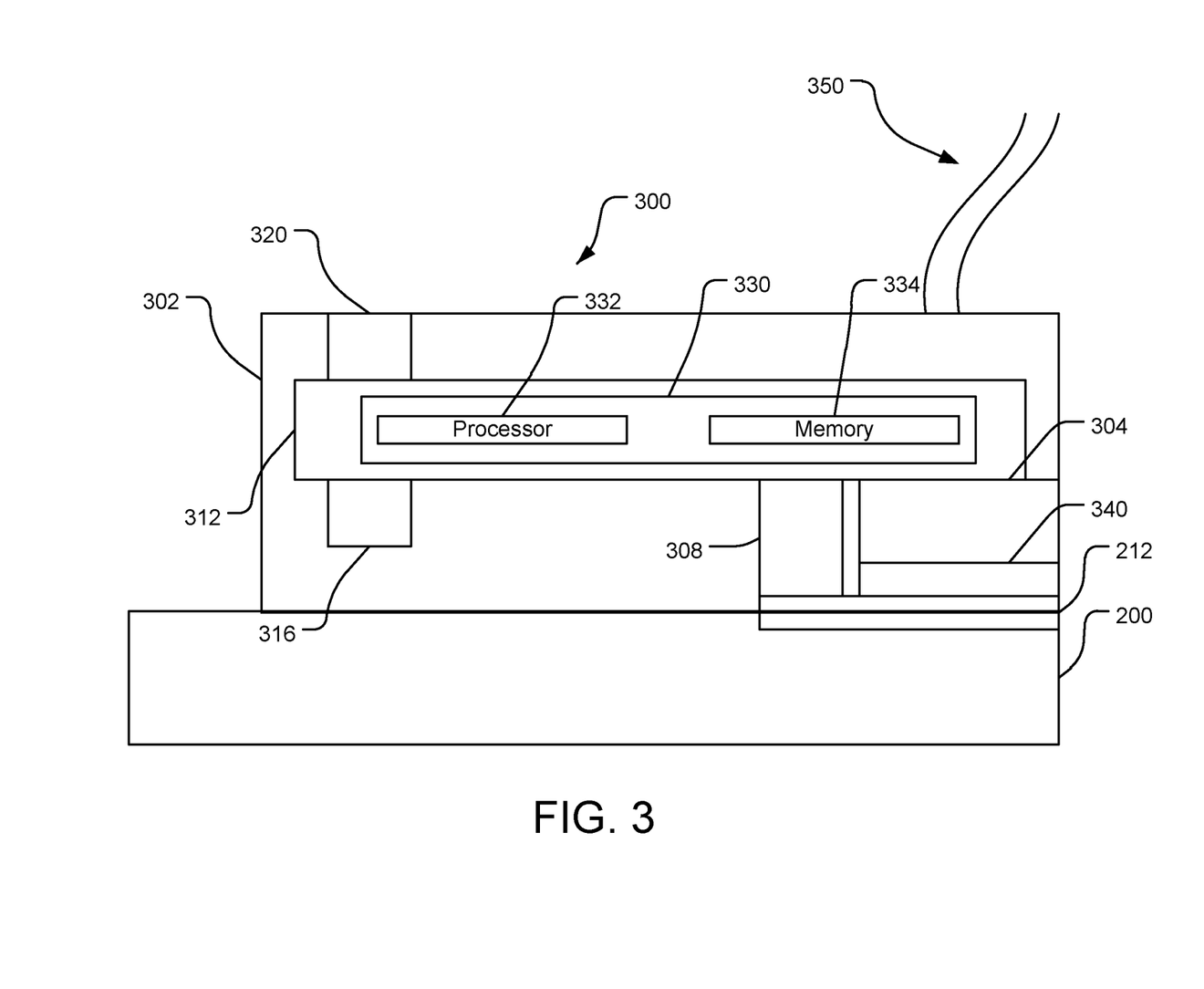
FIG. 3 is a block diagram illustrating a pump and pressure sensing module of the distributed NPWT system of FIG. 1, according to an exemplary embodiment.

The fluid interface 212 can couple the wound dressing module 200 to the pump and pressure sensing module 300, such as to allow fluid to flow from the wound dressing module 200 to a pump of the pump and pressure sensing module 300 (due to negative pressure applied by the pump to the fluid interface 212). The fluid interface 212 can include a filter that is at least one of hydrophobic or configured to filter bacteria. For example, the fluid interface 212 can include a GORE MMT314 filter.

The wound dressing module 200 includes a thermal dissipation layer 220, in some embodiments. The thermal dissipation layer 220 can include at least one of a metal coated mesh (e.g., silver coated, copper coated) or a perforated film mesh. The thermal dissipation layer 220 can increase heat dissipation from the at least one pump 304 of the pump and pressure sensing module 300, including to increase an evaporation rate of fluid in the wound dressing module 200.

Pump and pressure sensing module 300 can draw a vacuum at wound site 106 (relative to atmospheric pressure) by removing wound exudate, air, and other fluids from wound site 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 106 may include instillation fluid previously delivered to wound site 106. Instillation fluid can include, for example, a cleansing fluid, a prescribed fluid, a medicated fluid, an antibiotic fluid, or any other type of fluid which can be delivered to wound site 106 during wound treatment.

In some embodiments, the pump and pressure sensing module 300 includes at least one pump 304 and a pressure sensor 308. Pump 304 can be at least one of a displacement pump or a shockwave pump. Pump 304 can be a piezoelectric pump. In some embodiments, pump 304 includes a movable member (e.g., diaphragm) which undergoes mechanical displacement based on a voltage applied to the movable member, such as by oscillating in response to receiving an alternating current. By oscillating, the movable member can push air to generate the negative pressure applied by pump 304. The movable member can be metallic. Pump 304 can include a copper disc with a slit which opens when pushed by the movable member. In some embodiments, the movable member oscillates at an oscillation rate between approximately 13 kHz and 21 kHz. Under typical operational conditions, pump 304 can operate silently or near silently. For example, noise generated by pump 304 can be less than a noise threshold which can be heard by a typical user. In an embodiment, pump 304 is a Vacuum Pump manufactured by Koge Micro Tech Co., Ltd. Pump 304 can apply negative pressure to fluid interface 212 to draw fluid from the wound dressing module 200 via the fluid interface 212. Pressure sensor 308 can be protected from condensed fluid contact by the fluid interface 212.

The pump and pressure sensing module 300 includes an electronics module 312. The electronics module 312 can be flexible, such as a flexible circuit board to which electronic components can be mounted. The at least one pump 304 and the pressure sensor 308 can be mounted to the electronics module 312. The pump and pressure sensing module 300 can include a housing 302 that at least partially encloses the at least one pump 304, the pressure sensor 308, and the electronics module 312. The housing 302 can be attached to the wound dressing module 200.

In some embodiments, the pump and pressure sensing module 300 includes one or more sensors 316 mounted to the electronics module 312. The one or more sensors 316 can include a temperature sensor, such as a thermistor. The one or more sensors 316 can include a position sensor, such as an accelerometer. The one or more sensors 316 can include a pH sensor.

Figure 4:
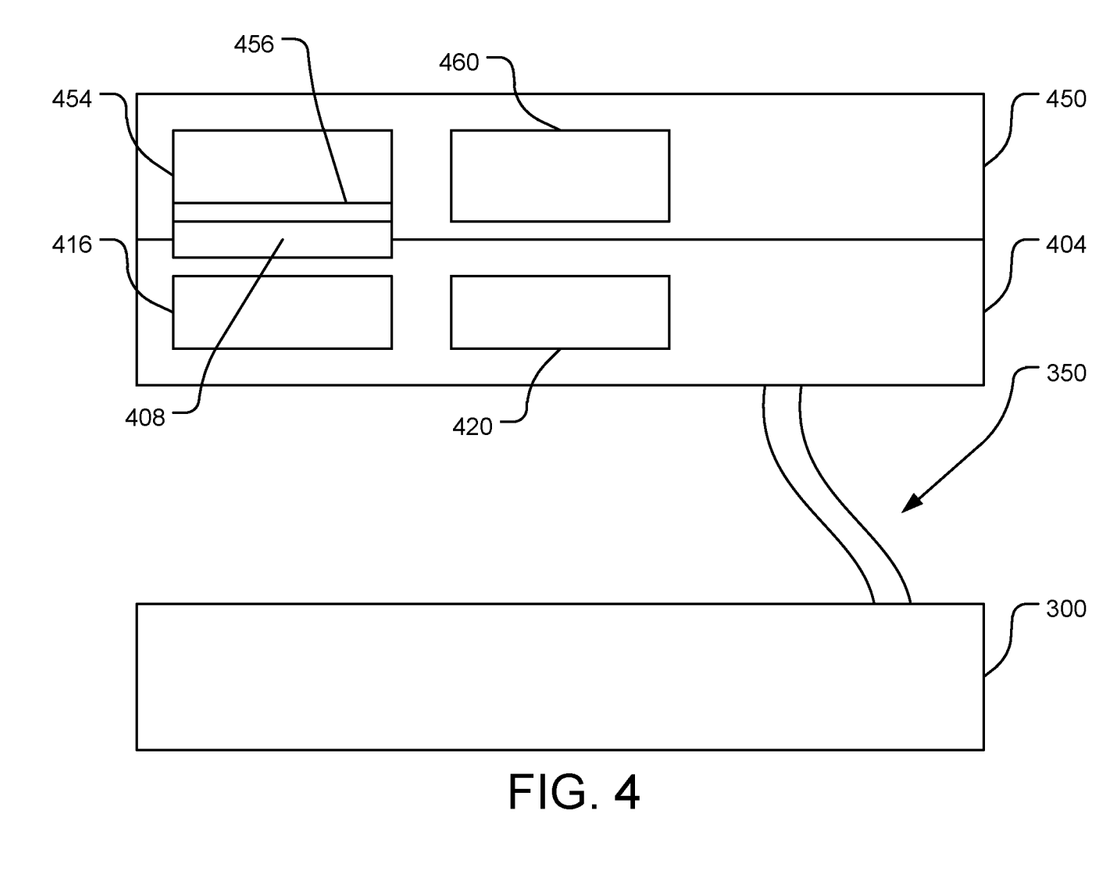
FIG. 4 is a block diagram illustrating a control and power module of the distributed NPWT system of FIG. 1, according to an exemplary embodiment.

An electrical coupler 350 connects the electronics module 312 to the control and power module 400. The electrical coupler 350 can be removably coupled to at least one of the electronics module 312 or the control and power module 400. The electronics module 312 can transmit, via the electrical coupler 350, at least one electrical signal indicating a status parameter to the control housing, the status parameter including at least one of a pressure, a temperature, an orientation, or a pH. The electrical coupler 350 can include a conductive wire ribbon. By connecting the electronics module 312 to the control and power module 400 to transmit information and power, the electrical coupler 350 can enable the control and power module 400 to be remote from and separate from the pump and pressure sensing module 300 (e.g., remote from the housing 302), and thus enable to pump and pressure sensing module 300 to be relatively lightweight. The electrical coupler 350 may have a minimum length to enable the control and power module 400 to be remote from and separate from the pump and pressure sensing module 300. The minimum length may greater than or equal to three inches, in some embodiments. The minimum length may be less than or equal to twenty four inches, in some embodiments.

The pump and pressure sensing module 300 can include a status indicator 320. The status indicator 320 can indicate a status of the NPWT system 100 based on information from electronics module 312, such as an indication of improper pump operation or other such problems with therapy delivery. The status indicator 320 can include one or more lights configured to output signals in at various wavelengths (e.g., colors).

Figure 1:
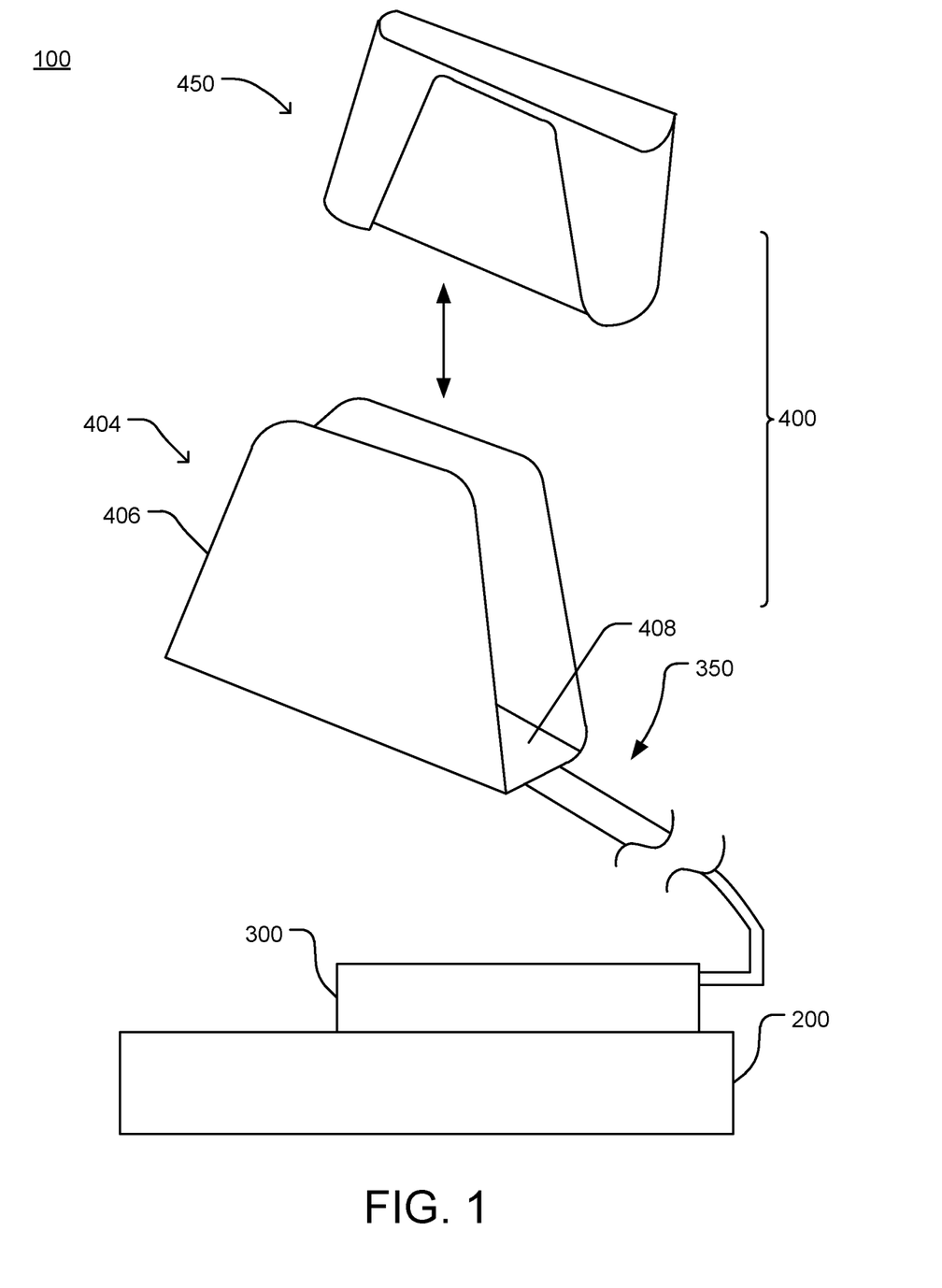
FIG. 1 is a schematic diagram of a distributed negative pressure wound therapy (NPWT) system, according to an exemplary embodiment.

The NPWT system 100 can include an exhaust interface 340. The exhaust interface 340 can be coupled to the at least one pump 304. The exhaust interface 340 can receive exhaust air from the at least one pump 304. The exhaust interface 340 can transfer the received exhaust air outside of the housing 302. The exhaust interface 340 can transfer the exhaust air to the wound dressing module 200 to increase a temperature of the wound dressing module 200, which can increase a rate of evaporation of fluid in the wound dressing module 200. The wound dressing module 200 an include a fluid transfer layer (e.g., a reticulated foam and thin PU film) to increase a rate of moisture transport through the wound dressing module 200; the exhaust interface 340 and fluid transfer layer can cooperate to reduce a load on the at least one pump 304 when the at least one pump 304 is operating to address a leak condition.

In some embodiments, the control and power module 400 includes a control housing 404 and a power housing 450. The control housing 404 and power housing 450 can be remote and separate from the housing 302 of the pump and pressure sensing module 300 (e.g., outside of the housing 302), enabling the pump and pressure sensing module 300 to be relatively lightweight and to avoid transfer of heat generated by the electronic components of the control and power module 400 to the wound dressing 200.

The electrical coupler 350 can be connected to the control housing 404 to provide information from the electronics module 312 (e.g., the at least one electrical signal) to the control housing 404. As shown in FIG. 1, the control housing 404 includes a first receiver body 406 in which the power housing 450 can be received; the power housing 450 may also receive the control housing 404. The first receiver body 406 defines a power reception interface 408, which can be an electrical interface that can be coupled to a power delivery interface 456 of the power housing 450 to receive electrical signals from the power housing 450 and transmit electrical signals to the power housing 450. The control housing 404 can be relatively small and/or lightweight, such as by not including any electro-mechanical components. The control housing 404 can be removably coupled to a corresponding connection component attachable to the patient, which can allow for modularity of and ease of use of NPWT system 100. For example, the connection component can include an adhesive breathable pad to be coupled to the control housing 404, and which can be replaced to reduce or eliminate trauma to the patient.

The electronics module 312 can include a processing circuit 330. The processing circuit 330 can generate the at least one electrical signal for transmission to the control and power module 400. The processing circuit 330 can include a processor 332 and a memory 334. Processor 332 may be a general purpose or specific purpose processor, an application specific integrated circuit (ASIC), one or more field programmable gate arrays (FPGAs), a group of processing components, or other suitable processing components. Processor 332 is configured to execute computer code or instructions stored in memory 334 or received from other computer readable media (e.g., CDROM, network storage, a remote server, etc.).

Memory 334 may include one or more devices (e.g., memory units, memory devices, storage devices, etc.) for storing data and/or computer code for completing and/or facilitating the various processes described in the present disclosure. Memory 334 may include random access memory (RAM), read-only memory (ROM), hard drive storage, temporary storage, non-volatile memory, flash memory, optical memory, or any other suitable memory for storing software objects and/or computer instructions. Memory 334 may include database components, object code components, script components, or any other type of information structure for supporting the various activities and information structures described in the present disclosure. Memory 334 may be communicably connected to processor 332 via processing circuit 330 and may include computer code for executing (e.g., by processor 332) one or more processes described herein. When processor 332 executes instructions stored in memory 334, processor 332 generally configures processing circuit 330 to complete such activities. It will be appreciated that some or all the functions executed by processing circuit 330 may be executed by a remote computing device or a processing circuit of power and control module 400, such as a device for use by a clinician that is communicatively coupled to NPWT system 100.

The processing circuit 330 can process the at least one electrical signal to generate an output signal for transmission to the control and power module 400 via the electrical coupler 350. For example, the at least one electrical signal can indicate at least three status parameters, and the processing circuit 330 can convert the at least one electrical signal into a multiplexed signal for transmission to the power housing 450 via the electrical coupler 350. For example, a number of conductive pathways of the electrical coupler 350 can be greater than or equal to four and less than or equal to eight to provide a multiplexed signal from the processing circuit 330 to the power module 400.

In some embodiments, the NPWT system 100 includes a user interface 416. User interface 416 may include one or more buttons, dials, sliders, keys, or other input devices configured to receive input from a user. User interface 416 may also include one or more display devices (e.g., LEDs, LCD displays, etc.), speakers, tactile feedback devices, or other output devices configured to provide information to a user. In some embodiments, the pressure measurements recorded by pressure sensor are presented to a user via user interface 416. User interface 416 can also display alerts generated by processing circuit 410. User interface 416 can be implemented in the control housing 404 (e.g., providing a start/stop button and status indicator to the control housing 404).

Control and power module 400 can include data communications interface 420 (e.g., a USB port, a wireless transceiver, etc.) configured to receive and transmit data. Communications interface 420 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 420 can include a USB port or an Ethernet card and port for sending and receiving data via an Ethernet-based communications link or network. In another example, communications interface 420 can include a Wi-Fi transceiver for communicating via a wireless communications network or cellular or mobile phone communications transceivers. Data communications interface 420 can transmit information based on data received from electronics module 312 via electrical coupler 350.

The power housing 450 includes a power supply 454. The power supply 454 can deliver power to the pump and pressure sensing module 300 via the power delivery interface 456 of the power housing 450, the power reception interface 408 of the control housing 404, and the electrical coupler 350. The power supply 454 can include a high-energy density cell, such as lithium polymer. The power housing 450 can include an interface to receive power to recharge the power supply 454, such as a secondary coil which may be compliant with a standard recharge interface. The power supply 454 can be replaceable.

The power housing 450 can include an alarm circuit 460. The alarm circuit 460 can be coupled to the electrical coupler 350. The alarm circuit 460 can detect a load of the electrical coupler 350, such as an impedance load of the electrical coupler 350. The alarm circuit 460 can evaluate an alarm condition based on the detected load. The alarm condition can be based on whether the power housing 450 is in and activated state and is coupled to (or not coupled to) the at least one pump 304 via the electrical coupler 350.

Figure 5:
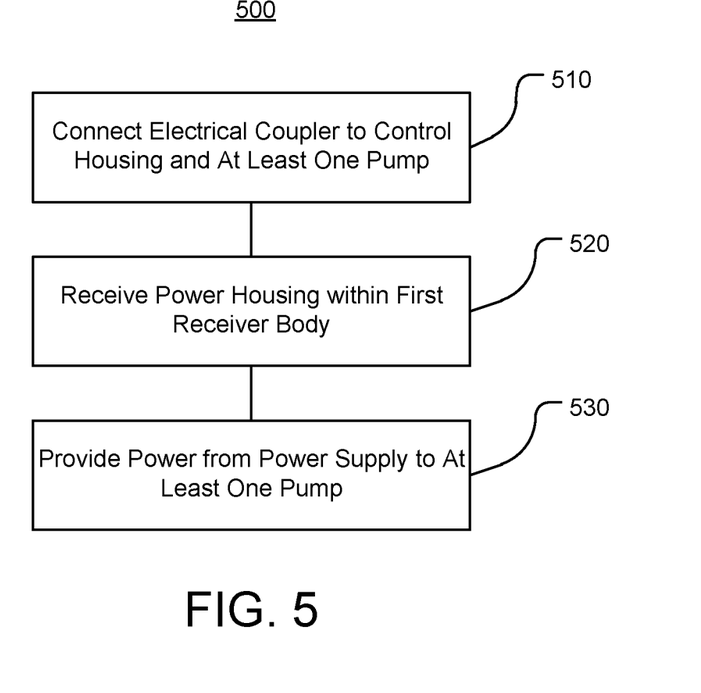
FIG. 5 is a flowchart of a process of operating the distributed NPWT system of FIG. 1, according to an exemplary embodiment.

Referring now to FIG. 5, a flowchart of a process 500 of operating a distributed NPWT system is shown, according to an exemplary embodiment. Process 500 can be performed by one or more components of NPWT system 100.

Process 500 is shown to include connecting an electrical coupler to a control housing and to at least one pump (step 802). The control housing can include a first receiving body defining a power reception interface. The at least one pump can be fluidly coupled to a fluid interface of a wound dressing to draw fluid from the wound dressing via the fluid interface. The wound dressing includes a sealing layer, an absorbent layer adjacent to the sealing layer, and a fluid interface attached to at least one of the sealing layer or the absorbent layer, in some embodiments.

Process 500 is shown to include receiving a power housing at least partially within the first receiver body to connect a power delivery interface of the power housing to the power reception interface of the first receiving body of the control housing (step 804).

Process 500 is shown to include providing power from a power supply of the power housing to the at least one pump via the power delivery interface, the power reception interface, and the electrical coupler (step 806).

In some embodiments, process 500 includes providing, by the power supply, power to a pressure sensor via the power delivery interface, the power reception interface, and the electrical coupler, the pressure sensor fluidly coupled to the wound dressing. The pressure sensor can detect a fluid pressure of the wound dressing (e.g., of fluid in the wound dressing). The pressure sensor can transmit a signal indicative of the fluid pressure to the control housing via the electrical coupler.

In some embodiments, process 500 includes outputting a status of the at least one pump. The status can be outputted using a status indicator coupled to the at least one pump.

Process 500 can include transmitting, from a first processing circuit attached to the wound dressing to a second processing circuit of the control housing via the electrical coupler, at least one electrical signal indicating a status parameter to the control housing, the status parameter including at least one of a pressure, a temperature, an orientation, or a pH. Transmitting the at least one electrical signal can include converting a plurality of status signals into a multiplexed signal.

In some embodiments, process 500 includes detecting, by an alarm circuit of the control housing, an impedance load of the electrical coupler. An alarm condition can be evaluated based on the impedance load, such as to determine if the power housing is in an activated state (e.g., providing power to the electrical coupler) but not coupled to at least one pump (which might result in undesired heat generation). An indication of an alarm condition can be outputted based on the impedance load indicating that the power housing is in an activated state and is not coupled to the at least one pump by the electrical coupler.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A negative pressure wound therapy system, comprising:
   a wound dressing module comprising:
      a sealing layer, an absorbent layer adjacent to the sealing layer, and a fluid interface attached to at least one of the sealing layer or the absorbent layer;
   a pump and pressure sensing module disposed on the wound dressing module, the pump and pressure sensing module comprising:
      at least one pump fluidly coupled to the fluid interface, the at least one pump configured to apply negative pressure to the fluid interface to draw fluid from the wound dressing via the fluid interface, and
      a pressure sensor fluidly coupled to the wound dressing module, the pressure sensor configured to detect a fluid pressure of the wound dressing module; and
   a control and power module removably coupled to and remote from the pump and pressure sensing module, the control and power module comprising:
      a control housing,
      an electrical coupler configured to connect the control housing to the at least one pump, and
      an alarm circuit configured to detect an impedance load of the electrical coupler and output an indication of an alarm condition based on the impedance load indicating that the control and power module is in an activated state and is not coupled to the at least one pump by the electrical coupler.

2. The negative pressure wound therapy system of claim 1, wherein:
   the control housing includes a first receiver body defining a power reception interface; and
   the control and power module includes a power housing sized to be at least partially received within the first receiver body of the control housing, the power housing including a power delivery interface configured to removably couple to the power reception interface of the control housing and a power supply configured to provide power to the at least one pump via the power delivery interface, the power reception interface, and the electrical coupler.

3. The negative pressure wound therapy system of claim 1, wherein the at least one pump and the pressure sensor are mounted to a flexible electronics module.

4. The negative pressure wound therapy system of claim 3, wherein the flexible electronics module includes at least one of a thermistor, an accelerometer, or a pH sensor.

5. The negative pressure wound therapy system of claim 3, wherein the flexible electronics module includes a status indicator.

6. The negative pressure wound therapy system of claim 3, further comprising a housing configured to at least partially enclose the flexible electronics module, the at least one pump, and the pressure sensor, the housing attached to the wound dressing module, the control and power module separate from and outside the housing.

7. The negative pressure wound therapy system of claim 6, further comprising an exhaust interface configured to receive exhaust air from the at least one pump and at least one of (1) transfer the received exhaust air outside of the housing or (2) transfer the exhaust air to the wound dressing to assist evaporation of fluid in the wound dressing.

8. The negative pressure wound therapy system of claim 1, wherein the electrical coupler is configured to transmit at least one electrical signal indicating a status parameter to the control housing, the status parameter including at least one of a pressure, a temperature, an orientation, or a pH.

9. The negative pressure wound therapy system of claim 7, wherein at least one electrical signal indicates at least three status parameters, the negative pressure wound therapy system further comprising a processing circuit configured to receive the at least one electrical signal and convert the at least one electrical signal into a multiplexed signal for transmission to the control and power module via the electrical coupler.

10. The negative pressure wound therapy system of claim 1, wherein the electrical coupler includes a conductive wire ribbon.

11. The negative pressure wound therapy system of claim 1, wherein the control and power module includes a communications circuit configured to output a communication signal based on data received via the electrical coupler.

12. The negative pressure wound therapy system of claim 1, wherein the control and power module comprises a power supply having a capacity sufficient to cause the at least one pump to output a vacuum pressure of at least 100 mmHg for a duration of at least 6 hours and a leak condition of at least 20 cubic centimeters per minute.

13. The negative pressure wound therapy system of claim 1, wherein the control housing includes a recharge interface operably connected to a power reception interface.

* * * * *